United States Patent
Beumer et al.

(10) Patent No.: US 9,383,326 B2
(45) Date of Patent: Jul. 5, 2016

(54) ONLINE MONITORING OF CONTAMINANTS IN CRUDE AND HEAVY FUELS, AND REFINERY APPLICATIONS THEREOF

(75) Inventors: Albertus Beumer, Saratoga Springs, NY (US); Zewu Chen, Schenectady, NY (US)

(73) Assignee: X-RAY OPTICAL SYSTEMS, INC., East Greenbush, NY (US)

( * ) Notice: Subject to any disclaimer, the term of this patent is extended or adjusted under 35 U.S.C. 154(b) by 189 days.

(21) Appl. No.: 14/127,646

(22) PCT Filed: Jun. 14, 2012

(86) PCT No.: PCT/US2012/042390
§ 371 (c)(1),
(2), (4) Date: Jan. 28, 2014

(87) PCT Pub. No.: WO2012/177472
PCT Pub. Date: Dec. 27, 2012

(65) Prior Publication Data
US 2014/0198898 A1    Jul. 17, 2014

Related U.S. Application Data

(60) Provisional application No. 61/498,889, filed on Jun. 20, 2011.

(51) Int. Cl.
*G01N 23/223* (2006.01)
*G01N 33/28* (2006.01)

(52) U.S. Cl.
CPC .......... *G01N 23/223* (2013.01); *G01N 33/2823* (2013.01); *G01N 2223/076* (2013.01); *G01N 2223/1003* (2013.01); *G01N 2223/637* (2013.01); *G01N 2223/652* (2013.01)

(58) Field of Classification Search
USPC ...................... 378/4, 6, 44, 45, 46, 47, 48, 49
See application file for complete search history.

(56) References Cited

U.S. PATENT DOCUMENTS

| 5,529,684 | A | 6/1996 | Greaney et al. |
| 7,477,724 | B2 | 1/2009 | Meier et al. |
| 2006/0093086 | A1 | 5/2006 | Gallagher |
| 2007/0295648 | A1* | 12/2007 | Falkiner ............... G01N 33/287 208/246 |
| 2009/0213988 | A1* | 8/2009 | Chen ..................... G01N 23/223 378/47 |

OTHER PUBLICATIONS

International Search Report for PCT/US2012/042390 dated Jan. 23, 2013.

\* cited by examiner

*Primary Examiner* — Nicole Ippolito
(74) *Attorney, Agent, or Firm* — Jeffrey Klembczyk, Esq.; Kevin P. Radigan, Esq.; Heslin Rothenberg Farley & Mesiti P.C.

(57) ABSTRACT

A technique, including associated method and system, for on-line measurement of a trace element in a crude or heavy fuel stream for a refinery, including in one embodiment: providing at least one x-ray fluorescence ("XRF") analyzer at a point for the refinery; analyzing the petroleum stream for chlorine using the analyzer; and providing results from the analyzer to refinery operators, to improve refinery operations. The analyzer may be a monochromatic wavelength XRF analyzer, wherein the analyzer focuses energy to/from the stream using an x-ray engine having at least one focusing, monochromating x-ray optic. The analyzer may be an MWDXRF or ME-EDXRF analyzer; and the trace element may be one or more of the following elements: S, Cl, P, K, Ca, V, Mn, Fe, Co, Ni, Cu, Zn, Hg, As, Pb, and Se; and in one embodiment the stream is crude, and the trace element is chlorine.

20 Claims, 5 Drawing Sheets

ONLINE MONITORING OF CONTAMINANTS IN CRUDE AND HEAVY FUELS, AND REFINERY APPLICATIONS THEREOF

CROSS-REFERENCE TO RELATED APPLICATION

This application is a continuation of PCT Application PCT/US2012/042390, filed Jun. 14, 2012, and published under the PCT Articles in English as WO 2012/177472 A2 on Dec. 27, 2012. PCT Application PCT/US2012/042390 claims the benefit of U.S. provisional patent application Ser. No. 61/498,889, filed Jun. 20, 2011, which is hereby incorporated herein by reference in its entirety.

TECHNICAL FIELD

The present invention relates in general to a real-time, on-line sample flow and analysis system for contaminant monitoring in crude oils and other heavy fuels, for refining applications.

BACKGROUND OF THE INVENTION

Fuel contaminants such as sulfur, chlorine, vanadium, and others present major regulatory and refinery process burdens for crude oils and heavy fuels, and there are currently no adequate on-line analyzers to measure these contaminants. This disclosure relates to a real-time, on-line sample flow and analysis system for contaminant monitoring in crude oils and other heavy fuels, for refining applications. By measuring these contaminants real-time, fuel refineries will benefit from extended overall uptime, increased process efficiency, and improved safety.

The presence of trace levels of contaminants in petroleum feedstocks is a growing problem in petroleum refining. Sulfur is a common component in crude oil streams—and its removal from final product is mandated due to its impact on the environment, as regulated by the US EPA under the Clean Air Act. Sulfur is harmful to the environment, and the cost of its removal is high. Therefore, monitoring sulfur levels early in the refining process is important.

Chlorine and vanadium contaminants are considered "bad actors" by the refining industry for primarily non-regulatory, process control reasons. In a 2004 industry white paper produced by the Crude Oil Quality Group, these contaminants were included in a group of eight contaminants of most concern to the industry.

Chlorides pose one of the greatest problems to the refining industry. According to a 2005 paper by The National Association of Corrosion Engineers ("NACE"): "Recently, an increasing number of refineries have experienced extreme corrosion and fouling in crude distillation unit overheads and/or naphtha hydrotreating units. The root causes were traced to severe spikes in the chloride levels."

Most chloride salts in crude oil are inorganic (sodium, magnesium, or calcium chloride) and can be effectively removed by a desalter. The nonextractable chlorides are not removed in the desalter, and can break down from downstream heating and processing to form hydrochloric acid, causing corrosion and fouling problems. The 2005 NACE paper documented over 20 cases of chloride damage to production facilities. It has also been reported that the chlorides collect in certain confined areas of various refinery systems, therefore multiplying their corrosive affects, even if the input levels are low. The NACE report also stated the extent to which refiners must monitor this problem: "Some companies called for [a maximum of] 5 ppm, while others called for 0 ppm organic chlorides. Typically, most companies called for from 1 to 3 ppm. From a corrosion point of view, the upper limit of 3 ppm is too high—a more realistic limit is 1 ppm . . . . Other companies flatly reject any and all crude oils containing organic chlorides in any amount." (NACE International Publication 34105)

Because chlorides are problematic, refiners may actually preclude the use of certain feedstocks due to the risk of unknown chloride levels. And, as the world's more desirable sources of crude oil are depleted, less pure crude is becoming more common. These sources are likely to have more salts, or higher sulfur content, that will require monitoring.

Chlorides may not only be naturally introduced, but also may arise from process sources. These sources include: chemicals used in enhanced oil recovery processes; chlorinated solvents used in crude oil production, transportation and storage; chlorinated additives used in production, transportation, and storage (possibilities include wax crystal modifiers, biocides, corrosion inhibitors, flocculation additives, and emulsion breakers); and/or the mixing of crude oil byproducts (slop) or other materials with new crude for purchase on the open market as a way to (illegally) boost sales and dispose of waste.

While most of these sources of chloride contamination are outside the control of the refinery, they all have implications for the refinery process at the input, process, and output stages.

In another challenge, the element Vanadium deactivates cracking catalysts. Also, when products containing vanadium are burned, corrosion of turbine blades may occur. According to the Crude Oil Quality group, off-specification coke may be produced when levels of vanadium are too high in crude oil. Technical Challenge—Sample Handling For On-Line Measurement of Crude and Heavier Fuels:

Any proposed on-line measurement techniques for low level contaminants in upstream crude flows, or other heavy fuels in this industry, must confront certain technical challenges.

Common trace analysis methods include chemical techniques such as titration, ion and gas chromatography, microcoulometry, and combustion spectroscopy. There are limitations to these methods. The first limitation is the low limit of quantification (LOQ) necessary. Process control in the petroleum industry may call for a LOQ of 0.5 ppm or less for chlorine. None of these methods provides a LOQ below 1 ppm except microcoulometry, but microcoulometry requires frequent calibration and cumbersome maintenance, and is a difficult method to use. Another limitation is that most of these techniques are laboratory-based methods and cannot be applied to online measurement due to complicated sample preparation and handling requirements. Finally, some of these methods may not measure all chlorides in a sample (e.g., gas chromatography).

Another major challenge is that most of these heavy upstream flows are "dirty" in an analytical sense, with viscosities not amenable to smooth flows through an analyzer. To accurately measure these contaminants online, consistent sample flows are necessary over a range of viscosities.

SUMMARY OF THE INVENTION

The shortcomings of the prior art are overcome and additional advantages are provided by the present invention which in one aspect is a technique, including associated method and system, for on-line measurement of a trace element in a crude or heavy fuel stream for a refinery, including in one embodiment: providing at least one x-ray fluorescence ("XRF") analyzer at a point for the refinery having the stream running therethrough; analyzing the petroleum stream for chlorine using the analyzer; and providing results from the analyzer to refinery or other operators, to improve refinery operations.

The analyzer may comprise a monochromatic optic enabled XRF analyzer, wherein the analyzer focuses energy to/from the stream using an x-ray engine having at least one focusing, monochromating x-ray optic. The analyzer may be an MWDXRF or ME-EDXRF analyzer.

The trace element may be one or more of the following elements: S, Cl, P, K, Ca, V, Mn, Fe, Co, Ni, Cu, Zn, Hg, As, Pb, and Se; and in one embodiment the stream is crude, and the trace element is chlorine.

The point in the refinery may be pre-desalter, post-desalter, hydrorefiners, and/or reformer; distillation unit, ADU, VDU, feed condenser, heat-exchanger, stripper, and/or hydrocracker; or may include feedstock areas prior to a refinery or other crude consuming operation, e.g., turbines.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in connection with the accompanying drawings in which:

DETAILED DESCRIPTION OF THE INVENTION

Two commercial technologies may be useful for online contaminant measurement of heavy samples. One is UV fluorescent (UVF) technology and the other is x-ray fluorescence (XRF). UVF methods are operator and maintenance intensive, requiring high-temperature furnace and gas utilities. An MWDXRF on-line analyzer (e.g., SINDIE/CLORA—discussed further below) is generally robust for clean, low-viscosity fuels (diesel/gasoline) but has challenges in upstream applications, such as crude-oil monitoring and feedstock pipeline blending—mainly because the x-ray window in the XRF analyzer can become contaminated by these "dirty" flows.
Monochromatic Wavelength Dispersive X-Ray Fluorescence (MWDXRF); and Monochromatic Excitation, Energy Dispersive X-Ray Fluorescence Analyzers (ME-EDXRF):

The assignee of the present invention has previously disclosed a Monochromatic Wavelength Dispersive X-ray Fluorescence (MWDXRF) on-line distillate analyzer using two monochromating optics (U.S. Pat. Nos. 6,934,359 and 7,072,439—hereby incorporated by reference herein in their entirety), shown schematically as system 10 in FIG. 1a. The related SINDIE (Sulfur IN DIEsel) product line for the measurement of sulfur in diesel fuel and other fuel distillates provides many advantages including: (1) signal/background (S/B) is improved due to monochromatic excitation of the sample by DCC1, i.e., the bremsstrahlung photons with energies under fluorescence peaks (which normally swamp these peaks of interest) can only reach the detector through scattering, therefore improving the S/B ratio dramatically compared to polychromatic excitation; (2) superior energy resolution—this eliminates all common interference problems and provides the physical basis for upstream applications; (3) inherent robustness and low maintenance—the analysis engine is low power, compact, with no moving parts or consumable gasses; and (4) unprecedented dynamic range, e.g., a quantification level from 0.3 ppm to 5% of sulfur in a sample.

Figure 1A:
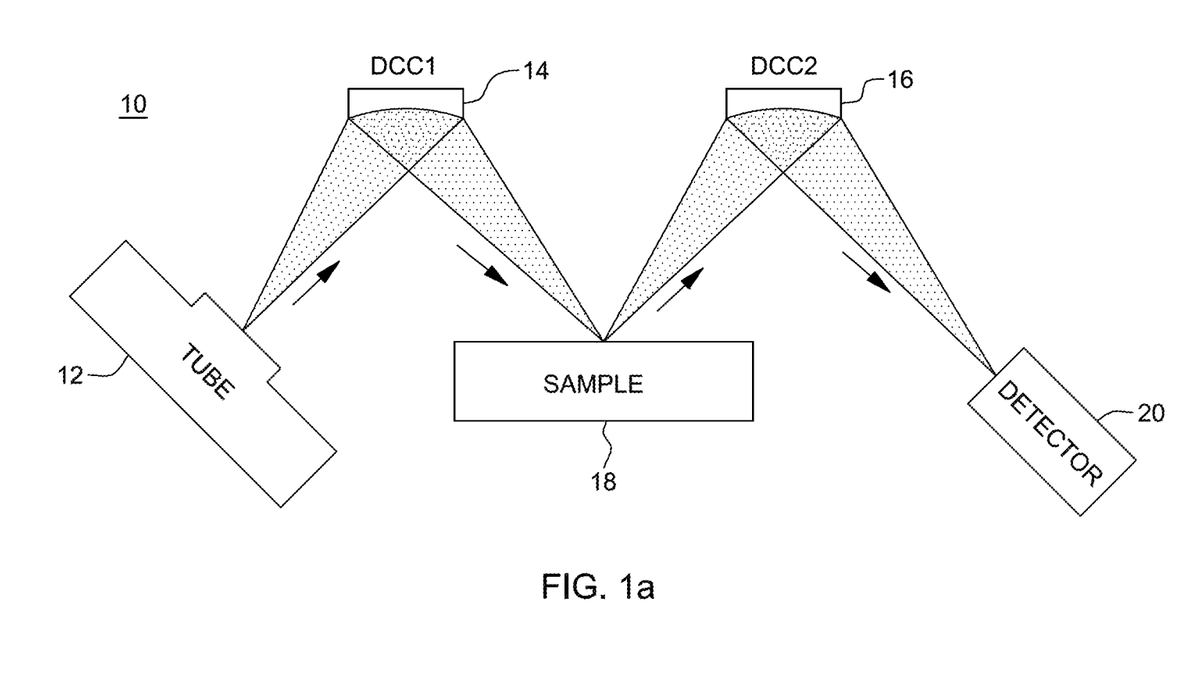
FIG. 1a depicts in schematic form an x-ray optic-enabled, MWDXRF analyzer.

The doubly curved crystal (DCC) optics 14, 16 in MWDXRF direct an intense micron-sized monochromatic x-ray beam from the tube 12 to the sample 18 to the detector 20 enhance conventional wavelength-dispersive XRF. These 3-D shaped optics selectively focus a very narrow band of x-ray wavelengths for sample excitation, according to Bragg diffraction laws.

One bench-top implementation is specifically designed for batch testing from 0.15-10,000 ppm (wt.) sulfur fuel samples at petroleum pipeline terminals, refineries, and test laboratories. One on-line implementation is an industrial grade process sulfur analyzer designed for continuous sulfur monitoring in diesel, gasoline and other clean distillates at, e.g. pipeline terminals, to monitor fuel interface cuts and tank contamination prevention where measurement speed and reliability and minimal maintenance are essential requirements. The concentration of e.g., sulfur can be constantly updated every 10 to 300 seconds, depending on the application.

A similar MWDXRF bench-top analyzer enables the user to quantify chlorine concentration below 0.5 ppm levels, without the difficulties of consumable gases or elevated temperature processes. Using the same MWDXRF technique as the SINDIE analyzers, this CLORA bench-top analyzer implementation provides a limit of chlorine detection of 0.15 ppm and a dynamic range up to 4%.

Figure 1B:
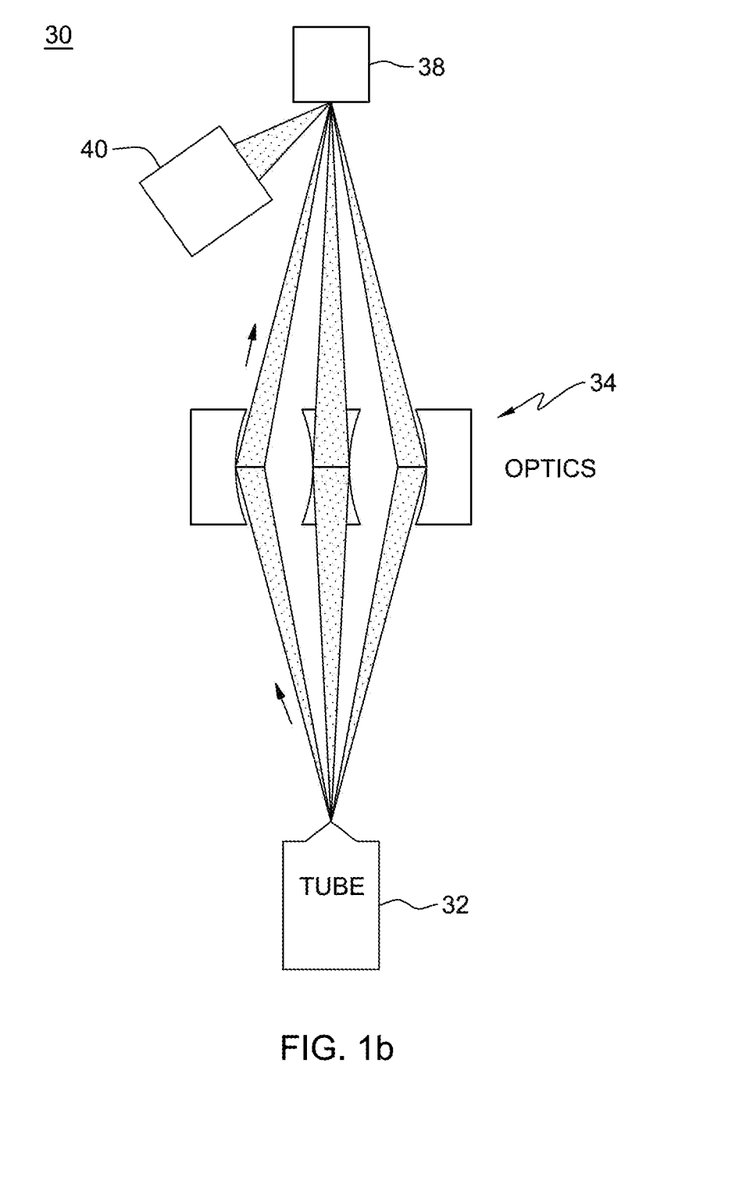
FIG. 1b depicts in schematic form an x-ray optic-enabled, ME-EDXRF analyzer.

On-line, monochromatic excitation, energy dispersive x-ray fluorescence (ME-EDXRF) analyzers can also be used for this application, in accordance with the present invention. The engine technology is disclosed in, e.g., commonly assigned PCT Publication No, WO 2009111454 (A1) entitled XRF System Having Multiple Excitation Energy Bands In Highly Aligned Package, the entirety of which is hereby incorporated by reference herein. In one embodiment this technique involves monochromatic excitation known as HDXRF system 30 as depicted schematically in FIG. 1b. HD XRF is a multi-element analysis technique offering significantly enhanced detection performance over traditional ED or WD XRF. This technique applies state-of-the-art monochromating and focusing optics 34 which focus x-rays from the tube 32 to sample 38, enabling multiple select-energy excitation beams that efficiently excite a broad range of target elements in the sample, which can be detected by, e.g., an energy-dispersive detector 40, which can detect the presence of one or more elements simultaneously. Monochromatic excitation dramatically reduces scattering background under the fluorescence peaks, greatly enhancing elemental detection limits and precision. HDXRF is a direct measurement technique and does not require consumables or special sample preparation.

The x-ray optics in either of these systems may include, for example, curved crystal monochromating optics such as those disclosed in commonly assigned U.S. Pat. Nos. 6,285,506; 6,317,483; 7,035,374; and 7,738,629; and/or multilayer optics; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506; 7,209,545; and 7,257,193 are also useable. Polarizing optic arrangements which provide a monochromating effect can also be used. Each of the above-noted patents is hereby incorporated herein by reference in its entirety.

Sample Cell and Flow Control Improvements:

In an on-line analyzer for crude and heavy fuel applications, pressure, temperature, and other flow characteristics in the flow cell should be dynamically controlled to maintain proper sample flow under varying sample conditions. Differing sample stream viscosities make it challenging to present samples to the analyzer at a stable pressure. Chlorine measurement presents another challenge because the chlorine mostly exists in water phase, which may not mix homogeneously in crude.

Improvements to the sample cell to address these challenges are disclosed herein. The sample cell may have a primary thin (e.g., Kapton) x-ray window to allow x-rays in and out of the cell. The window may be controlled, and in one embodiment separated, from the flow stream to minimize background and contamination. The goal is to present the sample to the XRF engine homogeneously with positioning accuracy at 20 microns—independent of the sample's incoming characteristics.

Proper sensors for temperature, pressure, flow rate, etc. and proper locations for those sensors, have been determined. Some components, such as redundant filters with self purging mechanical mixing, air removal, and pressure or flow regulators, may be placed at proper locations to optimize their effect on the whole system. A control algorithm may be implemented to handle the dynamics of the system in real-time without pre-knowledge of sample type. This improved system provides two simultaneous and important features: (1) a homogenous, predictable sample stream, along with (2) an x-ray focal area properly positioned. Together, these provide the ability to prepare and control different sample streams, e.g., different grades of crude.

Figure 2:
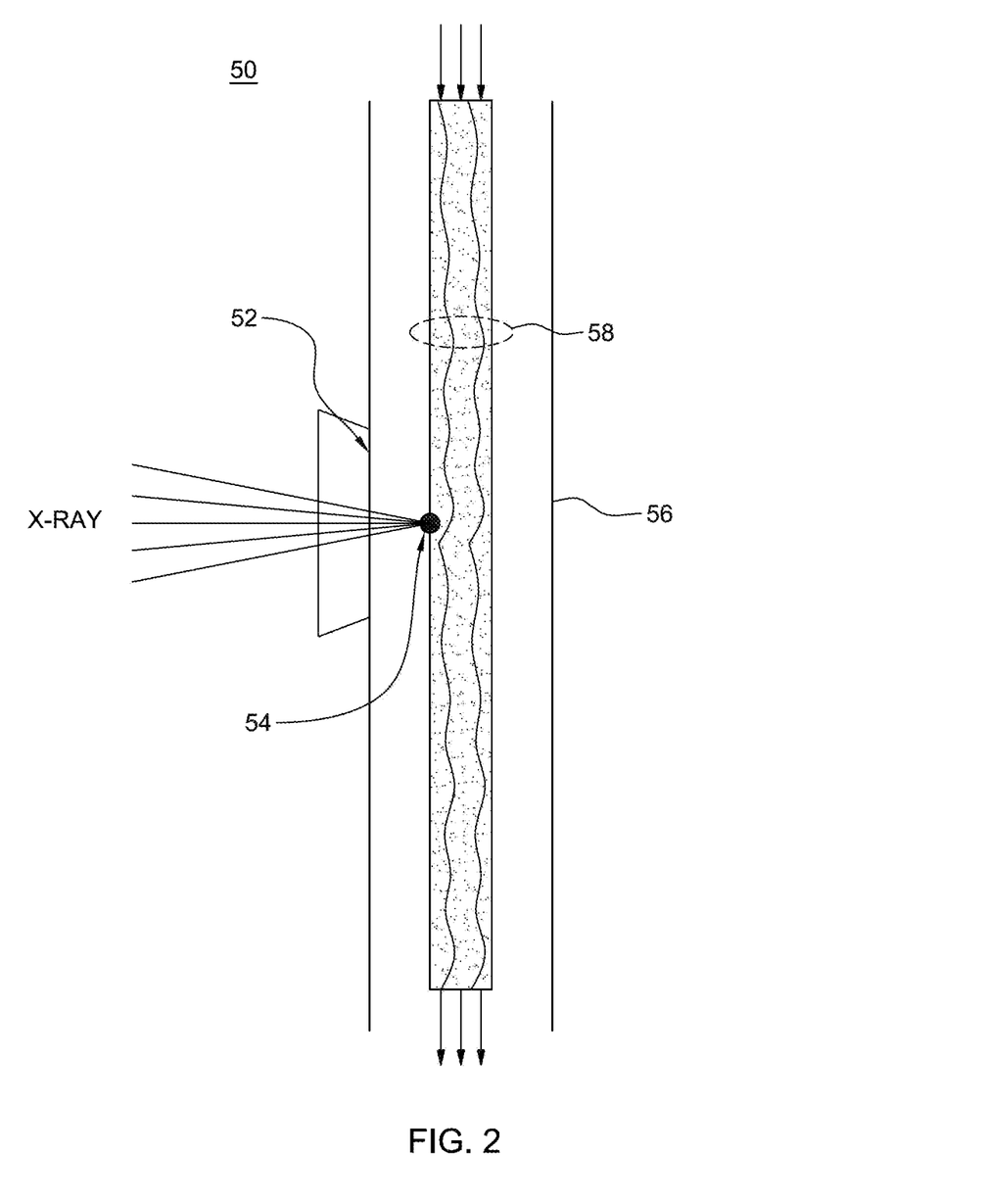
FIG. 2 depicts in schematic form an improved sample stream handling apparatus for an x-ray analyzer.

One component of a heavy-fuel measurement system requiring close attention is the sample barrier that allows x-rays to excite a heavy sample, while at the same time maintaining the vacuum in the x-ray engine and the flow pressure of a continuously-moving sample. X-ray stimulation may create e.g., sulfur ionization and adsorption at this interface over time and on certain types of barrier materials—leading to undesired sulfur residue and degradation of the barrier's x-ray transparency. XOS's dynamic window module ("DWM") as disclosed in U.S. Pat. No. 7,277,527 entitled "Movable Transparent Barrier For X-Ray Analysis Of A Pressurized Sample" (hereby incorporated by reference herein in its entirety) addresses this particular problem inherent in flowing petroleum sample streams. The DWM offers a very important and successful solution in the form of a moveable barrier advanced at programmable intervals to clean portions of a window roll. Other progress toward addressing this problem includes advance flow control mechanisms (e.g., Sample Module With Sample Stream Spaced From Window, For X-Ray Analysis System filed as PCT/US09/34982 and U.S. Ser. No. 12/391,677 now issued U.S. Pat. No. 8,050,382; and Sample Module with Sample Stream Supported and Spaced from Window, for X-Ray Analysis System filed as PCT/US11/24004 and U.S. Ser. No. 13/023,111; and Sample Viscosity and Flow Control for Heavy Samples, and X-Ray Analysis Applications Thereof filed as U.S. Ser. No. 61/523,605. Each of these patents/patent applications is hereby incorporated by reference herein in its entirety). In one such embodiment 50 shown schematically in FIG. 2, the sample stream is suspended as a laminar flow 58 within a sample chamber 56 and not in contact with the x-ray window 52. The sample stream surface is directly within the focal point 54 of the x-ray beam, and the window is out of focus.

Specifications for the improved on-line analyzers (including but not limited to ME-EDXRF and MWDXRF) may include but are not limited to:

Elements measured: S, Cl, P, K, Ca, V, Mn, Fe, Co, Ni, Cu, Zn, Hg, As, Pb, and/or Se.
Sample T>cloud point, max 250 deg. F.
Viscosity 20 cSt or more
Filtration: 100 um
LOD: 0.3 ppm @ 300 s—aqueous matrix
LOD: 0.2 ppm @300 s—hydrocarbon matrix
Analysis Time: 10-900 s—user adjustable
Range: 0.2 ppm/wt-3,000 ppm/wt One of the key benefits of the disclosed on-line analyzer is its ability to measure both organic and inorganic chlorides. And, due to a required distillation step, one of the restrictions of the existing ASTM method for measuring organic chlorides, is its inability to identify chlorinated materials with distillation temperatures above 400° F. The disclosed on-line analyzer would not share this limitation and could therefore be used to measure heavier molecular weight organic chlorides directly in distillates and/or crude oil.

Refinery Applications—e.g., Chlorine:

The improved on-line analyzers disclosed herein can be used as a diagnostic tool in a wide range of petroleum refining applications in accordance with the present invention, especially for, e.g., chlorine ("Cl") issues discussed above. All along the production line Cl levels may require monitoring in a wide range of samples including raw crude, partially processed crude, crude processing materials (water, refining chemicals), distilled product, and finished product. The present invention provides on-line monitoring at these process points. In this capacity the analyzer is essentially an inorganic Cl (salt) and/or organic CL detector. During the refining process, Cl salts turn into hydrochloric acid (HCl), gradually eroding the petroleum refining equipment. While there is a standard desalting process used, post desalted product can still contain 'phantom salts' that can damage equipment. Hence there is a need to test for Cl all along the process line.

Figure 3:
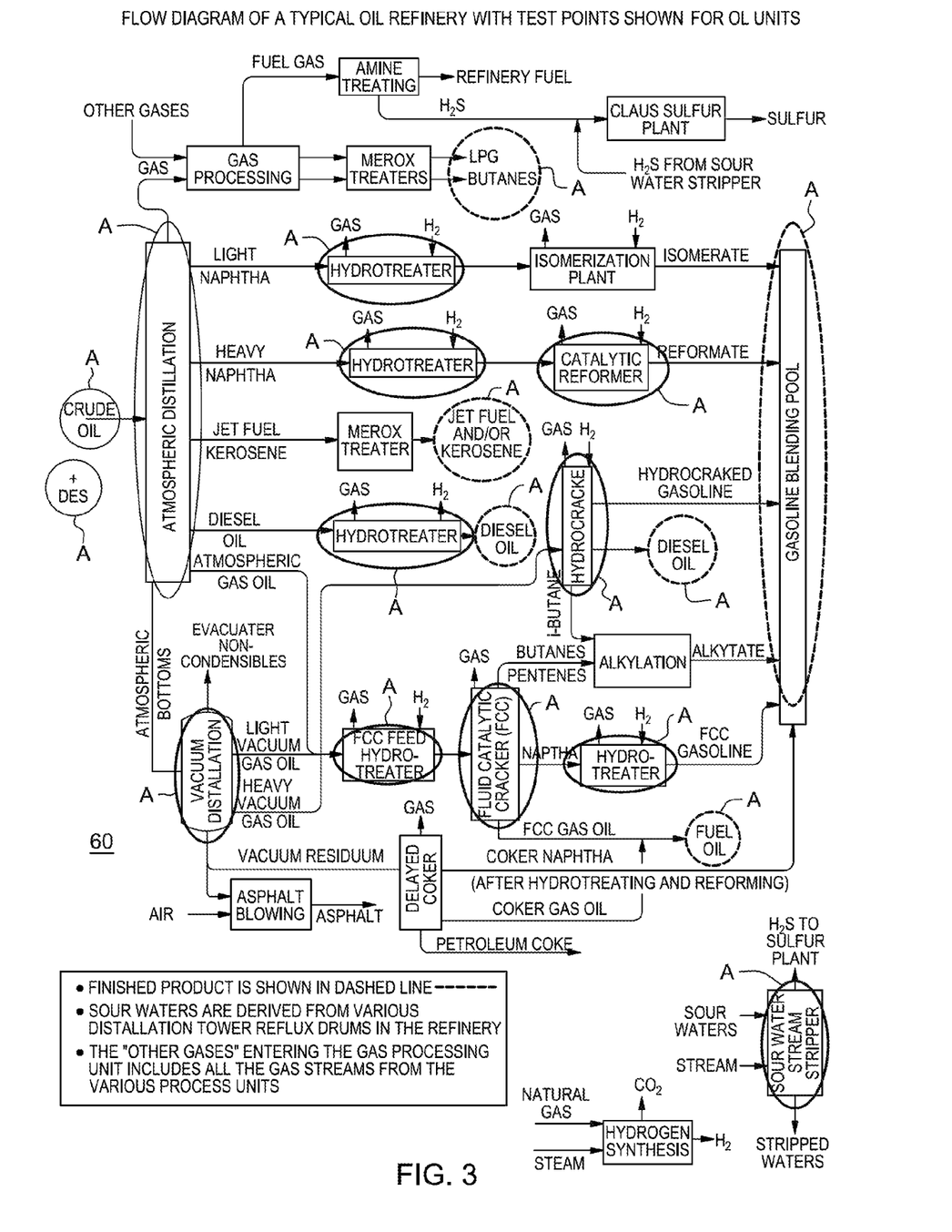
FIG. 3 depicts in schematic form a petroleum refinery and locations of on-line x-ray analyzers, in accordance with one or more aspects of the present invention.

FIG. 3 is a process flow diagram of a typical oil refinery 60, showing circles "A" depicting where chloride contamination is a problem and where the disclosed on-line analyzers may be deployed in accordance with the present invention to measure the process flows at these points. The thinner circles along the left represent the input of crude oil into the primary distillation process where the crude is broken into its constituent parts for further refining. It should be noted that the thin circle designation also encompasses the initial desalting operation discussed in detail below, in which water soluble chlorides are leeched from the crude. It is these areas where primary on-line detection of chlorides could occur. The thicker circles represent areas of the refinery operation that are susceptible to corrosion due to either the presence of non-desaltable chlorides (NDCs), and/or the introduction of Cl-containing catalysts/solvents; hence, these areas also present an opportunity for analyzer integration. Finally, the dashed circles represent finished product that may need to be tested for Cl based on either refinery or end-user specifications.

There are at least 19 potential points "A" of interest for on-line monitoring in accordance with the present invention, broken down approximately as follows:

1. NDC in desalted input crude,
2. in atmospheric distillation overheads,
3. in vacuum unit overheads,
4. in naphtha hydrotreater feeds/exchanges,
5. in hydrotreater stripper overheads,
6. in catalytic reformers,
7. in hydrocracker overheads,
8. in end product for shipment.

(These points may also include without limitation pre/post desalter unit, distillation unit, ADU, VDU, feed condenser, heat-exchanger, stripper, hydrocracker; or may include feedstock areas prior to a refinery or other crude consuming operation, e.g., turbines.)

Each of the above applications have different challenges and needs with respect to the sample to be tested, the inherent problems and costs of corrosive damage, and in the needed monitoring requirements. While some refiners have called special attention to NDC monitoring needs in naphtha hydrotreaters, others suggest that input monitoring of the desalted crude is the most important area to address.

Figure 4:
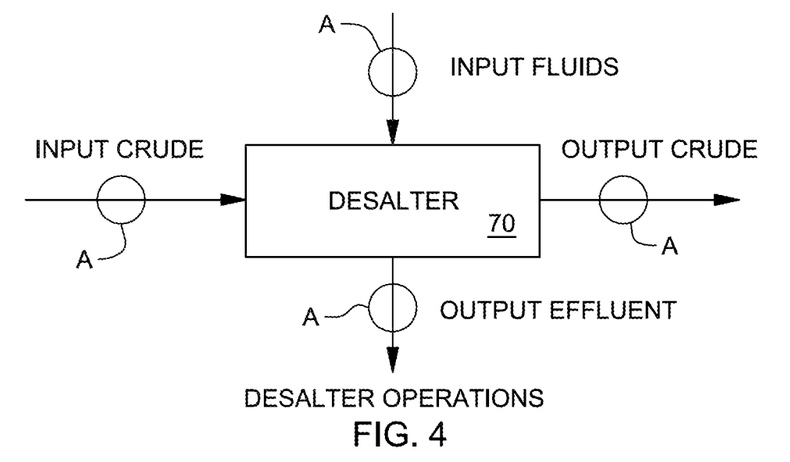
FIG. 4 depicts in schematic form a petroleum desalter and locations of on-line x-ray analyzers, in accordance with one or more aspects of the present invention.

Raw and Desalted Crude:

Using the analyzer to quantify chloride levels in both the raw and desalted crude is a key application of interest within the refining industry as schematically shown with respect to a sample desalter 70 as shown in FIG. 4 (where circles "A" are again used to denote points of use of on-line analyzers in accordance with the present invention). The ability to continuously monitor chloride content in desalted crude could be used to optimize desalter operation and crude unit overhead corrosion control programs, in accordance with the present invention.

There currently exist no on-line analyzers that can measure chlorides at the low ppm levels found in the crude oil pre-desalter and before entering the ADU. The ability to view real-time chloride results will give operators notice in case of a chloride spike, allowing the ability to divert the crude feed to tankage or take other steps to mitigate the damage. Besides the obvious human factors involved, these emergency situations involve the potential for serious environmental problems. The results of heater tube failures can result in crude oil and other hydrocarbons being released to the ground, air, and water. One example of where the proposed on-line chlorine measurement could be particularly beneficial is in the form of a dual-feed chlorine analyzer approach that automatically switches back and forth between the pre- and post-desalter stream to control and monitor the desalter operation. The benefits include optimization of the desalter resulting in lowered energy usage, increased worker safety, and reduction in unplanned shutdowns and loss of revenue, while decreasing additive usage.

Moreover, the operation of a modern desalter requires tremendous amounts of energy. The basic operation consists of high voltage current from passed over a number of plates or trays. Over and through these trays crude oil is heated by fuel gas and/or steam and flowed through a mixture of water and additives. By combining the water, voltage, and additives with the crude, the crude oil is washed of any "extractable" chlorides or salts. The salts in the water are then passed along to the waste-water plant for further treatment and discharge, the crude is pumped to the ADU, and the overhead gases are gathered for further treatment. By measuring and tightly controlling the chlorides during the removal process, the electricity, temperature, additives, and water can be controlled in a way that minimizes the utilities required and eliminates the over-treatment safety net that is the current industry norm.

With the added benefit of measuring organic chlorides, the analyzer addresses one of the ongoing concerns within the industry; that on some occasions, organic chlorides are present in crude and that these can hydrolyze to hydrochloric acid within the crude tower distillation unit. While this mechanism is the subject of some debate, the use of an instrument capable of detecting organic chlorides in crude would likely help resolve this issue.

Desalter Wash Water and Effluent:

Also, as shown in FIG. 4 with respect to the desalter, the use of the on-line analyzer in the desalter input wash and effluent water might also be of interest to some refiners. The results could be used to estimate/mass balance salt removal from the crude. Some refiners may also be interested in understanding the variations in chloride content of the desalter wash water, since the latter is usually composed of multiple water sources collected within the refinery.

Naphtha and Distillate Hydrofiners:

The primary objective of hydrofining is to remove sulfur and most nitrogen based components within a stream. During treating, metals and other contaminants will also be removed. For distillate and gas oil streams the goal is to reduce the sulfur content of blend stocks used in diesel fuel and/or downstream upgrading units. In the case of heavy naphtha, the primary objective of hydrotreating is to clean up the feed before sending it to the reformer.

The key concern with organic chlorides in refineries is its conversion to HCl within hydrofiners. Since as a rule, these units operate with very little water, there is a tendency to have any of the produced HCl accumulate in the very small water volumes present in the hydrofiner effluent. The end result is a severe drop in pH and aggressive corrosion of metallurgies. For this reason, ppm levels of organic chlorides in crudes can potentially be quite problematic.

ASTM D 4929 is limited in its ability to measure organic chlorides; to compounds with boiling points below 400° F. It is unable to provide any quantification of organic chlorides in heavier streams such as distillates or gas oils. Some refiners have reported evidence of organic chloride induced corrosion in distillate and gas oil hydrotreaters. The availability of equipment capable of measuring organic chlorides in both distillate and gas oil feeds would be beneficial. While these streams may be a little hotter than a typical target operability range, sample coolers could be employed to provide proper test conditions.

Reformer Light Ends:

Catalytic reforming is critical to the refinery, since it is used to manufacture reformate (octane booster), used in gasoline blending. Reformers use platinum/rhenium based catalysts that are susceptible to contamination by low levels of sulfur and other trace contaminants. Small halogenated hydrocarbons (organic chlorides) are added to the reformer feedstock (Heavy Virgin Naphtha) to acidify the catalyst surface and improve performance. On occasion, larger quantities are required to regenerate the catalyst. Product from the reformer will go to the aromatics extraction plant, gasoline blending, and light ends recovery.

Ironically the halogenated hydrocarbon used in the reformer is of the same chemistry type as the organic chlorides deemed problematic to hydrofiners. Even though this unit is located downstream of the hydrofiner, for efficiency reasons produced hydrogen is recycled back to the hydrofiner feed. Special efforts must therefore be made to insure that the organic chloride content of the recycle hydrogen is kept to a minimum to minimize corrosion issues in the hydrofiners. The other issue is that excess organic chlorides/HCL can escape in the reformate and attack downstream units (stabilizer tower).

The details surrounding the addition of maintenance and or regeneration levels of organic chlorides to the reformer feed is very catalyst/operation specific and often a closely guarded secret. Hence, whenever a chloride related corrosion issue surfaces in the downstream light ends recovery plant, the tendency is to blame the reformer, even though the light ends plant can receive feed from many different locations within the refinery. The installation of an on-line analyzer in the reformer product/light ends plant feed would help monitor reformer plant operation and potentially identify other chloride contributors.

Vanadium:

Finally, the effects of vanadium once identified can be mitigated by the use of additives or other means, but the vanadium level needs to be identified quickly. Vanadium contamination causes the catalyst to deactivate quickly resulting in the need to use more heat and energy to fire the process harder in order to reach the same level of cracking or conversion. These events also cause substantial waste of energy in the refinery. Problems with coking can result in unplanned shutdowns, similar to the issues discussed above with respect to chloride control and measurement. On-line measurement of vanadium in accordance with the present invention can mitigate these effects.

Figure 5:
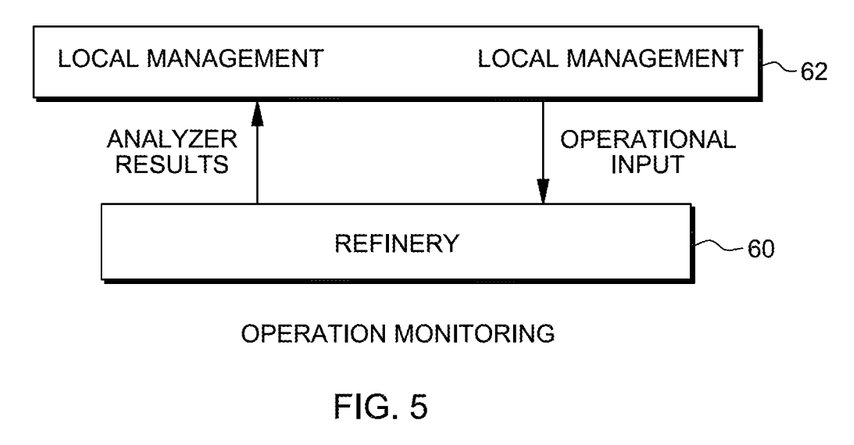
FIG. 5 depicts in schematic form the use of on-line analysis results by refinery management in accordance with one or more aspects of the present invention.

Refinery Operations:

Ultimately, the results from the on-line analyzers located throughout a refinery 60 can be used by local and remote management 62 of the refinery to improve its operational input and results, as shown in the flow diagram of FIG. 5.

The innovative, on-line petroleum analyzers discussed above provide a unique and valuable tool for the petroleum refining industry. By providing real-time measurement of a variety of contaminants (e.g., sulfur, chlorine, vanadium, and others) throughout a refinery, the safety, efficiency, and overall operational effectiveness of refineries can be dramatically improved.

As will be appreciated by one skilled in the art, one or more aspects of the present invention may be embodied as a system, method or computer program product. Accordingly, one or more aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, one or more aspects of the present invention may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

In one example, a computer program product includes, for instance, one or more non-transitory computer readable storage media to store computer readable program code means or logic thereon to provide and facilitate one or more aspects of the present invention.

Program code embodied on a computer readable medium may be transmitted using an appropriate medium, including but not limited to, wireless, wireline, optical fiber cable, RF, etc., or any suitable combination of the foregoing.

Computer program code for carrying out operations for one or more aspects of the present invention may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

One or more aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of one or more aspects of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the present invention may be provided, offered, deployed, managed, serviced, etc. by a service provider who offers management of customer environments. For instance, the service provider can create, maintain, support, etc. computer code and/or a computer infrastructure that performs one or more aspects of the present invention for one or more customers. In return, the service provider may receive payment from the customer under a subscription and/or fee agreement, as examples. Additionally or alternatively, the service provider may receive payment from the sale of advertising content to one or more third parties.

In one aspect of the present invention, an application may be deployed for performing one or more aspects of the present invention. As one example, the deploying of an application comprises providing computer infrastructure operable to perform one or more aspects of the present invention.

As a further aspect of the present invention, a computing infrastructure may be deployed comprising integrating computer readable code into a computing system, in which the code in combination with the computing system is capable of performing one or more aspects of the present invention.

As yet a further aspect of the present invention, a process for integrating computing infrastructure comprising integrating computer readable code into a computer system may be provided. The computer system comprises a computer readable medium, in which the computer medium comprises one or more aspects of the present invention. The code in combination with the computer system is capable of performing one or more aspects of the present invention.

Although various embodiments are described above, these are only examples. Further, other types of computing environments can benefit from one or more aspects of the present invention.

As a further example, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method of on-line measurement of a trace element in a crude or heavy fuel stream for a refinery, comprising:
   a. providing at least one x-ray fluorescence ("XRF") analyzer at a point for the refinery having the stream running therethrough, the point in the refinery being pre-desalter and/or post-desalter to monitor chlorine content in the stream to optimize desalter operation;
   b. analyzing the stream for the trace element using the analyzer; and
   c. providing results from the analyzer to refinery or other operators to improve operations.

2. The method of claim 1, wherein the analyzer comprises a monochromatic optic enabled XRF analyzer.

3. The method of claim 2, wherein the analyzer focuses energy to/from the crude stream using an x-ray engine having at least one focusing, monochromating x-ray optic.

4. The method of claim 3, wherein the analyzer comprises a window separating the x-ray engine from the crude stream.

5. The method of claim 1, wherein the analyzer is an MWDXRF or ME-EDXRF analyzer.

6. The method of claim 1, wherein the trace element is also at least one element chosen from the following list: S, Cl, P, K, Ca, V, Mn, Fe, Co, Ni, Cu, Zn, Hg, As, Pb, and Se.

7. The method of claim 1, wherein the stream is crude, and the trace element is chlorine.

8. The method of claim 1, wherein the point in the refinery comprises pre-desalter, post-desalter, hydrorefiners, reformer, and/or effluent discharge.

9. The method of claim 1, wherein the point in the refinery comprises pre/post desalter unit, distillation unit, ADU, VDU, feed condenser, heat-exchanger, stripper, and/or hydrocracker.

10. The method of claim 1, wherein the point in the refinery comprises additive addition and/or effluent discharge points.

11. A system for on-line measurement of a trace element in a crude or heavy fuel stream for a refinery, comprising:
   a. at least one x-ray fluorescence ("XRF") analyzer at a point for the refinery having the stream running therethrough, the point in the refinery being pre-desalter and/or post-desalter to monitor chlorine content in the stream to optimize desalter operation;
   b. wherein the stream is analyzed by the analyzer for the trace element chlorine; and
   c. wherein results from the analyzer are provided to refinery or other operators to improve refinery operations.

12. The system of claim 11, wherein the analyzer comprises a monochromatic optic enabled XRF analyzer.

13. The system of claim 12, wherein the analyzer focuses energy to/from the crude stream using an x-ray engine having at least one focusing, monochromating x-ray optic.

14. The system of claim 13, wherein the analyzer comprises a window separating the x-ray engine from the crude stream.

15. The system of claim 1, wherein the analyzer is an MWDXRF or ME-EDXRF analyzer.

16. The system of claim 1, wherein the trace element is also at least one element chosen from the following list: S, Cl, P, K, Ca, V, Mn, Fe, Co, Ni, Cu, Zn, Hg, As, Pb, and Se.

17. The system of claim 1, wherein the stream is crude, and the trace element is chlorine.

18. The system of claim 1, wherein the point in the refinery comprises pre-desalter, post-desalter, hydrorefiners, reformer, and/or effluent discharge.

19. The system of claim 1, wherein the point in the refinery comprises pre/post desalter unit, distillation unit, ADU, VDU, feed condenser, heat-exchanger, stripper, and/or hydrocracker.

20. The system of claim 1, wherein the point in the refinery comprises additive addition and/or effluent discharge points.

* * * * *